United States Patent [19]

Tomko

[11] Patent Number: 5,391,816
[45] Date of Patent: Feb. 21, 1995

[54] FORMATION OF 1-PHENYLVINYL-1-PHOSPHONIC ACID

[75] Inventor: John Tomko, Dobbs Ferry, N.Y.

[73] Assignee: Akzo Nobel N.V., Arnhem, Netherlands

[21] Appl. No.: 148,728

[22] Filed: Nov. 8, 1993

[51] Int. Cl.$^6$ ............................................. C07C 62/00
[52] U.S. Cl. ......................................................... 562/8
[58] Field of Search ............................................ 562/8

[56] References Cited

U.S. PATENT DOCUMENTS

| | | | |
|---|---|---|---|
| 2,694,684 | 11/1954 | Rogers et al. | 252/49.8 |
| 3,363,032 | 1/1968 | Fitch et al. | 562/8 |
| 3,931,294 | 1/1976 | Auel et al. | 562/8 |
| 4,316,859 | 2/1982 | Photis | 562/8 |
| 4,359,431 | 11/1982 | Magee, Jr. et al. | 562/8 |
| 4,486,357 | 12/1984 | Krause et al. | 562/8 |
| 4,507,249 | 3/1985 | Pieper et al. | 562/8 |
| 4,529,559 | 7/1985 | Pieper | 260/502.4 R |
| 4,692,282 | 9/1987 | Pieper | 260/502.4 R |
| 5,132,444 | 7/1992 | Northemann et al. | 562/8 |

FOREIGN PATENT DOCUMENTS

| | | | |
|---|---|---|---|
| 1318809 | 5/1973 | United Kingdom | C07F 9/38 |
| 2102427 | 2/1983 | United Kingdom | C07F 9/38 |

OTHER PUBLICATIONS

Derwent Patent Abstract 39482R, Oct. 28, 1967.
Derwent Patent Abstract 86–002165/01, Oct. 28, 1985.
Journal of the American Chemical Society vol. 44, pp. 2530–2536 (1922).

Primary Examiner—Marianne M. Cintins
Assistant Examiner—Keith Mac Miller
Attorney, Agent, or Firm—Richard P. Fennelly; Louis A. Morris

[57] ABSTRACT

A process for forming 1-phenylvinyl-1-phosphonic acid utilizes reacting a mixture of phosphorus trihalide, such as phosphorus trichloride, and acetophenone with water, under conditions in which the water is gradually added to the mixture with cooling to form a reaction mixture, which can be sparged of excess acetophenone with aqueous acid while under vacuum, comprising the 1-phenylvinyl-1-phosphonic acid. This product can be recovered from the reaction mixture by recrystallization from aqueous mineral acid, such as hydrochloric acid.

7 Claims, No Drawings

FORMATION OF 1-PHENYLVINYL-1-PHOSPHONIC ACID

BACKGROUND OF THE INVENTION

The present invention is an improved process for the synthesis of 1-phenylvinyl-1-phosphonic acid (PVPA), which can be polymerized to higher molecular weight species or processed with further polymerizable compounds in the manufacture of copolymers. Some representative references which describe how this well-known compound can be formed include the following: Conant et al. J. Amer. Chem. Soc. 44, 2530–2536 (1922), which shows the use of acetophenone, phosphorus trichloride, and glacial acetic acid as reagents; and U.S. Pat. No. 4,529,559, which shows the reaction of acetophenone, phosphorus trichloride, and water in Example 5 under heating conditions of up to 150° C. The temperature conditions used in the previously mentioned patent were used to remove residual acetophenone from the reaction mixture but they can lead to a lessened product yield due to the formation of dimeric and oligomeric by-products.

SUMMARY OF THE INVENTION

The present invention is a process for forming 1-phenylvinyl-1-phosphonic acid (PVPA) and comprises reacting a mixture of phosphorus trihalide, such as phosphorus trichloride, and acetophenone with water, under conditions in which the water is gradually added to the mixture with cooling to form a reaction mixture, which is sparged of excess acetophenone while under vacuum, comprising the 1-phenylvinyl-1-phosphonic acid. This product can be recovered from the reaction mixture which results from the sparging operation by recrystallization from a dehydrating acid, such as hydrochloric acid.

DESCRIPTION OF PREFERRED EMBODIMENTS

The present invention is advantageously practiced by first combining phosphorus trichloride and a molar excess of acetophenone which serves both as a solvent and reagent for the instant process. Approximately a one to two molar excess of the acetophenone is adequate. After these reagents have been allowed to become thoroughly mixed, preferably at ambient or room temperature, water is then gradually added, preferably dropwise, with sufficient cooling to preferably maintain the temperature in the range of from about 5° C. to about 60° C. The resulting reaction mixture will contain the desired PVPA product along with undesired excess, non-reacted acetophenone which must be removed.

The removal of the excess acetophenone is accomplished in accordance with the present invention by sparging the reaction mixture, while under vacuum, with an acid, such as aqueous HCl, which catalyzes the dehydration of the intermediate product initially formed, hydrolyzes any cyclic and/or oligomeric compositions which may contain P—O—P bonds and/or pyrophosphate linkages, and effectively entrains excess acetophenone at an attractively low temperature of below 100° C. minimizing temperature-generated by-product formation, to yield a subsequent reaction mixture containing the desired PVPA product in higher yield.

The desired product can be effectively recovered from the reaction mixture resulting from the sparging with the dehydrating acid by recrystallization from HCl. The use of HCl as a recrystallization agent has several advantages. For example, the acid component of filtrate resulting from such a recrystallization step can be treated with sodium hydroxide, forming salt and water as environmentally acceptable byproducts. The HCl is itself easily stripped from the desired product PVPA thereby further simplifying the ultimate the recovery of PVPA.

The present invention will be further understood by the Examples which follow.

EXAMPLE 1

Acetophenone (327.5 gm, 2.726 moles) and 249.9 gm (1.82 moles) of $PCl_3$ were placed into a nitrogen-blanketed 500 cc reaction flask and were allowed to stir at room temperature for one hour. The reactor was then vigorously stirred with ice/water cooling, and 49 gm (2.726 moles) of water were added dropwise starting at 7° C. and completed at 50° C. The total water addition time was fifty minutes. The reaction proceeded with formation of large amounts of HCl that were trapped in a caustic scrubber. When the HCl evolution subsided at 80°–85° C., vacuum was applied, and the reaction mixture was sparged with 2% HCl at 100° C. and water aspirator pressure for six hours and forty minutes.

The stripped crude reaction mixture contained 86.6 mol % of 1-phenylvinyl-1-phosphonic acid (PVPA) (by $^{31}P$ NMR) with 1.4% of acetophenone remaining (by G.C.)

The crude reaction mixture was then treated at 95° C. with 151 gm of 37% HCl (50% of the crude yield). The HCl addition took five minutes resulting in a temperature drop to 75° C. This mixture was then vigorously stirred and cooled in a water bath to 35° C. when it was seeded with a small amount of PVPA. Cooling continued to 25° C. (twenty minutes), and the resulting thick slurry was filtered through a coarse fritted funnel. The PVPA crystals were washed with 35 gm of 37% Hcl. The yield of the air-dried first crop was 58.2% (of theoretical yield), M.P. 109.5°–110° C.

EXAMPLE 2

Acetophenone (538.7 gm, 4.48 moles), 513 gm (3.74 moles) of $Pcl_3$, and 100.9 gm (5.605 moles) of water were reacted as described in Example 1. The reaction mixture was sparged with 2% HCl. for nine hours. The crude product contained 86.5 mol % of PVPA (by $^{31}NMR$) with 2.9% acetophenone remaining. Crystallization from 315 gm of concentrated HCl afforded 400 gm of (air-dried) PVPA (first crop), 58% of theory.

COMPARATIVE EXAMPLE 3

This Example was a repetition of the synthesis reaction shown in Example 5 of U.S. Pat. No. 4,529,559.

Acetophenone (158.3 gm, 1.3176 moles) and 150.7 gm (1.093 moles) of $PCl_3$ were placed into a nitrogen-blanketed 500 cc reaction flask and were allowed to stir at room temperature for two hours. Then, 29.6 gm (1.646 moles) of water were added into the vigorously stirred reactor in thirty-nine minutes. At this stage, the exotherm reached 43° C. The reactor was then heated to 100° C. in ten minutes. The reactor was then placed under vacuum of 12 mm Hg, and the excess acetophenone was distilled to 150° C. in one hour. The stripped residue was then hydrolyzed with 88 gm of water by heating to 100° C. in forty-five minutes. The results of $^{31}$P NMR analysis: 82.6 mole % PVPA; 7.6 mole % phosphorous acid; 0.6 mole % phosphoric acid; and other dimeric and oligomeric by-products.

The yield of PVPA in this Example in the stripped crude reaction mixture was inferior to that in Examples 1 and 2.

COMPARATIVE EXAMPLE 4

This Example was another repetition of the synthesis reaction shown in Example 5 of U.S. Pat. No. 4,529,559.

Acetophenone (217.8 gm, 1.813 moles) and 207.4 gm (1.51 moles) of PCl$_3$ were placed into a nitrogen-blanketed 500 cc reaction flask and were allowed to stir at room temperature for two hours. Then, 40.77 gm (2.265 moles) of water were added into the vigorously stirred reactor in fifty-three minutes while the temperature ranged from 24° C. to 75° C. The reactor was then heated to 110° C. in twenty-seven minutes. The crude reaction mixture was then placed under vacuum of 12 mm Hg, and 105° C.–150° C. for fifty-five minutes to remove excess acetophenone. The glassy stripped residue was then hydrolyzed with 121 gm of water at 100° C. in forty minutes. The hydrolysate was then stripped again at 12 mm Hg and 50° C. for one hundred and ten minutes. The results of 31P NMR analysis: 80.1 mole % PVPA; 4.4 mole % phosphorous acid; 0.7 mole % phosphoric acid; and other dimeric and oligomeric by-products.

The yield of PVPA in this Example in the stripped crude reaction mixture was inferior to that in Examples 1 and 2.

The foregoing Examples are presented for illustrative purposes only and, for that reason, should not be construed in a limiting sense. The scope of protection sought is set forth in the Claims which follow.

I claim:

1. A process for forming 1-phenylvinyl-1-phosphonic acid which comprises reacting a mixture of phosphorus trihalide and acetophenone with water, under conditions in which the water is added to the mixture with cooling, to form a crude reaction mixture which is then sparged, under vacuum, with an aqueous dehydrating acid, removing excess acetophenone, to form a subsequent reaction mixture comprising the 1-phenylvinyl-1-phosphonic acid product.

2. A process as claimed in claim 1 wherein the crude reaction mixture is sparged with aqueous hydrogen chloride.

3. A process as claimed in claim 1 wherein the phosphorus trihalide is phosphorus trichloride.

4. A process as claimed in claim 1 wherein the 1-phenylvinyl-1-phosphonic acid is recovered from the subsequent reaction mixture by recrystallization from aqueous mineral acid.

5. A process as claimed in claim 4 wherein the acid is hydrochloric acid.

6. A process as claimed in claim 1 wherein the subsequent reaction mixture is sparged with aqueous hydrogen chloride, the phosphorus trihalide is phosphorus trichloride, and the 1-phenylvinyl-1-phosphonic acid is recovered from the reaction mixture by recrystallization from aqueous mineral acid.

7. A process as claimed in claim 6 wherein the aqueous mineral acid is hydrochloric acid.

* * * * *